United States Patent [19]
Kress

[11] 3,956,301
[45] May 11, 1976

[54] PROCESS FOR BROMINATION OF PYRIMIDINE

[75] Inventor: Thomas J. Kress, Indianapolis, Ind.

[73] Assignee: Eli Lilly and Company, Indianapolis, Ind.

[22] Filed: Mar. 24, 1975

[21] Appl. No.: 561,140

Related U.S. Application Data

[63] Continuation-in-part of Ser. No. 308,389, Nov. 21, 1972, abandoned.

[52] U.S. Cl............................................. 260/251 R
[51] Int. Cl.² ...................................... C07D 239/30
[58] Field of Search ................................ 260/251 R

[56] References Cited
OTHER PUBLICATIONS

Bredereck et al., Chem. Ber. 91 pp. 2832–2848 (1958).
Bredereck et al., Chem. Ber. 95, pp. 803–808 (1962).
Tetrahedron Letters, 22, pp. 2183–2186 (1972).
Gilman, et al., J. Am. Chem. Soc. 69, p. 1946 (1947).
Rec. Tran. Chem. 84 pp. 1101–1108 (1965).
J. Org. Chem. 27, pp. 1318–1323 (1962).

*Primary Examiner*—Lewis Gotts
*Assistant Examiner*—D. R. Phillips
*Attorney, Agent, or Firm*—Dwight E. Morrison; Everet F. Smith

[57] ABSTRACT

The process for brominating pyrimidine which comprises reacting bromine at an elevated temperature with the hydrogen halide addition salt of pyrimidine in an organic solvent substantially inert to the action of bromine under the conditions of the process. The process is also shown to be applicable to other nitrogen-containing heterocycles.

6 Claims, No Drawings

PROCESS FOR BROMINATION OF PYRIMIDINE

CROSS-REFERENCE

This application is a continuation-in-part of copending application Ser. No. 308,389, filed Nov. 21, 1972, now abandoned.

BACKGROUND OF THE INVENTION

1. Field of the Invention

The compound, 5-bromopyrimidine, has proven to be a valuable intermediate in the synthesis of several new agricultural products, particularly those which have interesting growth regulator and fungicidal properties, as taught in Belgian Pat. No. 714,003. The importance of these products led to a search for a more facile synthesis of the important intermediate, 5-bromopyrimidine.

2. Description of the Prior Art

In the prior art, Bredereck et al., Chem. Ber. 91, 2832 at 2848 (1958), teach the reaction of pyrimidine hydrochloride with bromine by heating a mixture of the two in an oil bath for about 3 hours at a temperature of about 160°C., to form a solid mass, the reaction product mixture. The temperature of the oil bath was then raised to 250°C., and the 5-bromopyrimidine hydrobromide was sublimed out of the solid reaction product mixture under vacuum. The 5-bromopyrimidine hydrobromide was taken up in sodium bisulfite solution, the solution made alkaline with potassium hydroxide, and extracted with chloroform. The chloroform was distilled to leave behind pure 5-bromopyrimidine.

An alternate approach to the synthesis of 5-bromopyrimidine is also reported by Bredereck et al., Chem. Ber. 95, 803 at 807 and 808 (1962). 2-Bromo-1,1,3,3-tetraethoxypropane was prepared by brominating 1,1,3,3-tetraethoxypropane in carbon tetrachloride. The 2-bromo-1,1,3,3-tetraethoxypropane was then condensed with formamde, in the presence of ammonium formate and water, to give 5-bromopyrimidine.

Yet another method of preparation of 5-bromopyrimidine is described by van der Does, Tetrahedron Letters 22, 2183–2186 (1972), accomplished by bromination of pyrimidine in the gas phase at a temperature of from 220° to 500°C., optimally, 300°C., for a 35–40 percent yield of 5-bromopyrimidine.

The preparation of 4-bromoisoquinoline is taught by Gilman et al., J. Am. Chem. Soc. 69, 1946 (1947). Isoquinoline perbromide hydrobromide was subjected to prolonged heating, yielding a solid mass. Excess aqueous sodium hydroxide solution was added to the solid mass and the liberated 4-bromoisoquinoline was recovered by steam distillation. The crude product was purified by recrystallization from petroleum ether.

The preparation of 5-bromo-4-phenylpyrimidine via a six-step synthetic process is reported by van der Plas, Rec. Trav. Chim. 84, 1101 (1965), who stated that the direct bromination method of Bredereck et al., supra, did not seem suitable for the synthesis of 5-bromo-4-phenylpyrimidine, the phenyl group being vulnerable to the attack of brominating agents.

The preparation of 3-bromoquinoline by the pyrolysis of quinoline hydrobromide perbromide at 180°–200°C. is reported by Eisch, J Org. Chem. 27, 1318 (1962).

SUMMARY OF THE INVENTION

This invention relates to a process for brominating pyrimidine to yield 5-bromopyrimidine in good yield, which process is adaptable to commercial use. The process comprises adding bromine over a period of time to a heated mixture of pyrimidine, in the form of its hydrogen halide salt, and an aromatic organic solvent which is substantially inert to the action of bromine under the conditions of the reaction.

The process is also applicable to the bromination of other nitrogen-containing heterocycles selected from the group consisting of 4-phenylpyrimidine, quinoline, isoquinoline, and 1,6-naphthyridine.

DESCRIPTION OF THE PREFERRED EMBODIMENT

The preparation of a 5-bromopyrimidine is conveniently carried out using a hydrogen halide addition salt of pyrimidine selected from the group consisting of pyrimidine hydrochloride, pyrimidine hydrobromide, and pyrimidine hydriodide. Pyrimidine hydrochloride is the pyrimidine hydrogen halide addition salt of choice for use in the process.

The pyrimidine hydrogen halide is suspended in a suitable reaction solvent, the mixture heated, and bromine is added thereto. The bromine and the pyrimidine hydrogen halide appear to first form a complex, which complex is soluble in the reaction solvent. The solvent selected for use is substantially inert to the action of bromine under the conditions of the reaction. A suitable reaction solvent is one in which the starting pyrimidine hydrogen halide addition salt is insoluble, the complex formed between the bromine and the pyrimidine hydrogen halide addition salt is quite soluble, and in which the 5-bromopyrimidine hydrogen halide addition salt, the product, is substantially insoluble.

Suitable and desirable solvents for use in the novel process include organic aromatic compounds such as nitrobenzene, o-dichlorobenzene, chlorobenzene, o-nitrotoluene, and benzonitrile. These organic aromatic compounds, which act as solvents in this reaction process, are substantially inert to the action of bromine under the conditions of the novel process. The starting pyrimidine hydrogen halide is insoluble in these organic aromatic solvents, the complex formed between the pyrimidine hydrogen halide and bromine is quite soluble in these organic aromatic solvents, and the 5-bromopyrimidine hydrogen halide addition salt is substantially insoluble in these organic aromatic solvents.

These organic aromatic solvents are also preferred because of their ease of handling and possibilities for recycling. Of the solvents named above, nitrobenzene, o-dichlorobenzene, benzonitrile, and o-nitrotoluene are also particularly helpful in obtaining improved yields of the desired 5-bromopyrimidine. Of these organic aromatic solvents, nitrobenzene, o-dichlorobenzene and benzonitrile are preferred, with nitrobenzene being the solvent of choice.

In addition to the advantages conferred upon the reaction by the solvent, as described above, the solvent provides other beneficial effects to the novel process. The solvent assists in controlling the temperature of the reaction mixture, and allows better mixing of the bromine and the pyrimidine hydrogen halide addition salt, and permits the reaction to be run at a lower temperature than expected from teachings of the prior art. The solvent permits the reaction mixture to be stirred throughout the duration of the reaction. This reaction product mixture which can be stirred is in marked contrast to those described in the prior art where the reaction product mixtures set up as solid masses as the reaction proceeded. The presence of the solvent also makes isolation of the 5-bromopyrimidine product easier. With the solvent present, the reaction product mixture is present in the reaction vessel as a slurry instead of a solid mass at the completion of the reaction, and the crude product can be filtered off from the solvent. This is more convenient, especially on a large-scale run, than isolating the product either by sublimation or by chiseling it out of the reaction vessel. The presence of the solvent thus greatly aids in making large-scale preparations feasible.

The bromination reaction is carried out by suspending the hydrogen halide addition salt of the pyrimidine in the organic aromatic solvent, for example, nitrobenzene, and heating the mixture to a suitable temperature, namely from about 125° to about 135°C.

The bromine is added to the heated mixture over a period of from about 30 to about 90 minutes. The addition is preferably carried out at such a rate that a smooth and controlled reaction of bromine with the pyrimidine is accomplished. The addition of the bromine over the period of about 30 to about 90 minutes can preferably be accomplished dropwise in the laboratory. It is preferred that addition of the bromine be accomplished in equal portions at evenly spaced intervals of time, but addition of unequal portions of bromine may also be accomplished at unequal intervals of time.

As the bromine is added, hydrogen halide is evolved from the reaction mixture. The rate of evolution of the hydrogen halide is regulated by the rate of addition of the bromine. Control of the rate of evolution of the hydrogen halide is important in one aspect in that too rapid evolution of hydrogen halide may produce entrainment of the bromine being added. Such entrainment can cause loss of bromine, and cut down the yield of product, while raising the cost of production. Control of the rate of evolution of the hydrogen halide is important in another aspect in that the effluent gas from the reaction is desirably put through a scrubber to remove the hydrogen halide. Such removal is desirable in maintaining the atmosphere as free from noxious gases as possible. Thus, whether the reaction is being carried out on a laboratory scale or a commercial scale, the addition of the bromine is preferably accomplished at a rate which permits control of the rate of evolution of hydrogen halide to prevent the entrainment and loss of bromine, and which allows the efficient removal of hydrogen halide from the effluent gases produced by the reaction.

When addition of the bromine is complete, the reaction product mixture is heated for an additional period of time, about 2 to about 6 hours, to complete the reaction. Longer heating times tend to lower the yield of desired product and for that reason are to be avoided. Heating times also depend on the heterocyclic compound being brominated.

At the end of the additional heating period, the reaction product mixture is ready for work-up. The reaction product mixture is worked up by methods well known to those skilled in the art. Thus, the reaction product mixture is partially cooled, and a solvent, for example, benzene, added thereto. Other solvents which can be used include hexane, ether, toluene and xylene. The added solvent aids in diluting the reaction solvent and in separating the product from such solvent. After addition of the diluting solvent, the whole mixture is further cooled to about room temperature. The mixture is filtered to separate the solid which has precipitated upon cooling. The precipitated solid is the hydrogen halide salt of the 5-bromopyrimidine. The 5-bromopyrimidine free base is obtained by suspending the salt in water, adjusting the pH to approximately pH 8 to 10 with strong base, and steam distilling. Suitable strong bases include sodium hydroxide, potassium hydroxide, sodium carbonate, and the like. The product is filtered from the cooled distillate. Alternatively, the product can be recovered by extraction of the basic mixture with chloroform or ether, or the like. The chloroform or ether extract is dried and the solvent distilled in vacuo, to yield the 5-bromopyrimidine.

While the process has been described and directed particularly to the bromination of pyrimidine, it has been found to be also applicable to other nitrogen-containing heterocycles, including those selected from the group consisting of 4-phenylpyrimidine, quinoline, isoquinoline, and 1,6-naphthyridine. The same general procedure is employed in the bromination of each compound, with the temperature of reaction being varied depending on the compound being brominated, and the time of addition of the bromine being varied for the same reason.

The following Examples 1–4, inclusive, serve to illustrate the bromination of pyrimidine. The remainder of the examples serve to illustrate the application of the novel process to other nitrogen-containing heterocycles.

EXAMPLE 1

5-Bromopyrimidine

A slurry of 29.0 g. (0.25 mole) of pyrimidine hydrochloride in 30 ml. of nitrobenzene, contained in a 250 ml. three-neck round-bottom flask equipped with a paddle stirrer, condenser, dropping funnel, and thermometer, was heated to about 130°C., and 44.0 g. (0.275 mole) of bromine was added dropwise through the dropping funnel over a period of 30 minutes. Heating and stirring was continued at about 130°C., for an additional two hours. At the end of that time, the reaction product mixture was cooled to about 80°C., and 150 ml. of benzene was added. The resulting slurry was filtered. The solid collected on the filter was washed with 100 ml. of benzene, and sucked dry. The dry, tan solid, which weighed 61.0 g., was placed in 200 ml. of water. The aqueous mixture was adjusted to pH 8 with a saturated solution of sodium carbonate and steam distilled. The distillate was cooled and the white solid filtered therefrom and air-dried overnight. The aqueous filtrate was extracted three times with 100 ml. portions of ethyl ether. The combined ether extracts were dried, filtered, and evaporated to yield additional product which was combined with the previously recovered product. The product had a melting point of about 73°–75°C. and weighed 35 g. (88 percent of theory). It was identified by n.m.r. spectrum and elemental analyses as 5-bromopyrimidine.

Other solvents were used in the reaction as set forth in the following table.

| Example | Compound | Solvent | Temp. | Product | % Yield |
| --- | --- | --- | --- | --- | --- |
| 2 | Pyrimidine.HCL | benzonitrile | 125–128°C. | 5-bromopyrimidine | 80 |
| 3 | Pyrimidine.HCl | o-nitrotoluene | 130°C. | 5-bromopyrimidine | 71 |
| 4 | Pyrimidine.HCl | o-dichlorobenzene | 130°C. | 5-bromopyrimidine | 84 |

EXAMPLE 5

3-Bromoquinoline

A slurry of 33.3 g. (0.20 mole) of quinoline hydrochloride in 50 ml. of nitrobenzene, contained in a 250 ml. three-neck round-bottom flask equipped with a paddle stirrer, condenser, dropping funnel, and thermometer, was heated to 177°–180°C., and 35.2 g. (0.22 mole) of bromine was added dropwise via the dropping funnel over a period of 1½ hours. The temperature was maintained at about 180°C., and the mixture stirred for an additional 3 hours and 20 minutes, at which time the evolution of hydrogen chloride had ceased. Heating was stopped, the reaction product mixture was cooled to room temperature, and 200 ml. of benzene was added. The mixture was filtered, and the solid on the filter was washed with 100 ml. of benzene, and sucked dry on the filter. In this manner, 48.7 g. of crude product was obtained. This crude product was added to 200 ml. of water and the mixture made basic with saturated aqueous sodium carbonate solution. The basic mixture was extracted four times with 200 ml. portions of ether. The combined ether extracts were dried, and the solvent was removed in vacuo, leaving 35.1 g. of a pale yellow oil which solidified on standing in the refrigerator. The solid had a melting point of about 12°–13°C., and was identified as 3-bromoquinoline. Yield, 84.5 percent of theory; VPC purity, 97 percent.

EXAMPLE 6

4-Bromoisoquinoline

The same general procedure set forth in Example 1 above was followed. In a flask equipped with a reflux condenser, dropping funnel, thermometer, and stirrer was placed 33.3 g. (0.20 mole) of isoquinoline hydrochloride, together with 50 ml. of nitrobenzene, and the mixture was stirred and heated to about 180°C. to give a clear yellow solution. To this solution was added dropwise, via the dropping funnel, over a period of 1 hour and 13 minutes, 35.2 g. (0.22 mole) of bromine. The evolution of hydrogen chloride was smooth from the start to the completion of the addition of the bromine. After all the bromine had been added, the reaction mixture was of a single phase, amber red in color. Heating at about 180°C. and stirring were continued after addition of the bromine had been completed. An hour later, a few crystals of a solid material started to collect in the flask near the condenser. After 3 hours and 15 minutes of heating and stirring a very thin slurry of crystals had begun to form and hydrogen chloride evolution had become very slow. After 4 hours and 45 minutes of heating and stirring, the evolution of hydrogen chloride had practically ceased.

The heat source was shut off and the almost clear amber solution was allowed to cool slowly. At about 150°C., crystallization became very rapid. At about 90°C., 200 ml. of benzene was added to the slurry, and the mixture was stirred for about 15 minutes. The mixture was then cooled to about 20°C. and filtered to yield fine cottony needles which were washed with 100 ml. of benzene, then reslurried with 200 ml. of benzene, filtered off, and dried. The product, which weighed 46.6 g., was placed in 200 ml. of water and the mixture made basic by the addition of a saturated solution of sodium bicarbonate. The basic mixture was extracted four times with 200 ml. portions of ether. The combined ether extracts were dried over anhydrous magnesium sulfate. The drying agent was filtered off, and the ether was evaporated, to yield 33.6 g. of a pale yellow oil, which crystallized on standing. Using vapor-phase chromatography, this crude material was shown to contain 93.5 percent of 4-bromoisoquinoline. The overall yield of 4-bromoisoquinoline was about 80.5 percent. A sample of the crude material was recrystallized from petroleum ether to yield product having a melting point of about 41°–42°C.

EXAMPLE 7

5-Bromo-4-phenylpyrimidine

Following the same general procedure set forth above, a mixture of 11.0 g. (0.0572 mole) of 4-phenylpyrimidine hydrochloride in 30 ml. of nitrobenzene, contained in a three-neck flask equipped with stirrer, thermometer, condenser, and dropping funnel, was stirred and heated in an oil bath at about 150°C., and 9.2 g. (0.0575 mole) of bromine was added over a period of 35 minutes. Evolution of hydrogen chloride began immediately. The reaction mixture was heated and stirred about 5.5 hours at 150°C. after addition of the bromine.

At the end of that time the reaction product mixture was cooled to about 105°C. and 100 ml. of benzene was added. Cooling was continued and at about 47°C. a brown solid separated and a slurry formed. The mixture was stirred for about 20 minutes while cooling to room temperature. The solid material which separated was filtered off, and the filtrate, a mixture of nitrobenzene and benzene, was saved for further work-up. The gummy solid on the Buchner funnel was then suspended in water and the mixture made basic by the addition of 4.2 g. of 50 percent aqueous sodium hydroxide. The basic aqueous mixture was extracted with chloroform. The chloroform extracts were combined, dried over anhydrous magnesium sulfate, and evaporated, to give 6.1 g. of a gummy solid. By vapor-phase chromatography assay, the gummy solid was shown to consist of 71 percent of 4-phenylpyrimidine and 29 percent of the desired product, 4-phenyl-5-bromopyrimidine. An additional 5.9 g. of solid was recovered from the filtrate, referred to above, the combined benzene and nitrobenzene from the beginning work-up of the reaction product mixture. This additional solid material was assayed by vapor-phase chromatography and was determined to contain 39 percent starting 4-phenylpyrimidine and 61 percent 5-bromo-4-phenylpyrimidine.

EXAMPLE 8

3,8-Dibromo-1,6-naphthyridine

Following the same general procedure set forth in Example 1, a mixture of 9.8 g. (0.0589 mole) of 1,6-naphthyridine hydrochloride and 20 ml. of nitrobenzene was heated to 180°C. and bromine (10.36 g., 10 percent molar excess) was added dropwise over a period of about 50 minutes. When the addition of the bromine was complete, the reaction mixture was heated and stirred at about 178°–180°C. for an additional 3½ hours. The reaction product mixture was then cooled to about 90°C. and 100 ml. of benzene added thereto. A tan solid separated which was filtered off and washed with ether and benzene. The solid weighed about 15 g. This tan solid was added to about 100 ml. of water. The pH of the mixture was adjusted to about 8, using solid sodium carbonate, and the basic mixture extracted four times with 200 ml. portions of chloroform. The combined chloroform extracts were dried and were evaporated to dryness to yield 8.7 g. of a tan solid. Vapor-phase chromatography showed two major components, one of which was the free base of the starting 1,6-naphthyridine and the other appeared to be desired product. The crude product was chromatographed on grade 3 alumina using 5 percent ethyl acetate in carbon tetrachloride as solvent. By this procedure, there was obtained 4.4 g. of product which was identified by the n.m.r. spectrum as 3,8-dibromo-1,6-naphthyridine. This material was recrystallized from commercial absolute ethanol to yield 3.8 g. of needle-like crystals having a melting point of about 186°–188°C.

The bromo-substituted nitrogen-containing heterocycles, prepared as set forth above, are useful intermediates in the preparation of compounds having interesting pharmaceutical, veterinary, and agricultural chemical utilities. Thus, for example, the 5-bromopyrimidine is used in the synthesis of certain substituted 5-pyrimidinemethanols, which are useful either as fungicides for the control of numerous plant pathogenic fungi, or as plant growth regulators. As taught in Belgian Pat. No. 714,003, referred to supra, the synthesis of the 5-substituted pyrimidinemethanols in accomplished by reaction of a ketone with 5-bromopyrimidine in the presence of n-butyllithium at the low temperature of a Dry Ice-acetone cooling bath.

The 4-bromoisoquinoline can be used in the preparation of 4-sulfanilamidoisoquinoline, useful for its antistreptococcal properties, as reported by Craig and Cass, *J. Am. Chem. Soc.* 64, 783 (1942).

The 3-bromoquinoline can be used in the preparation of α-(2-piperidyl)-3-quinolinemethanol, as reported by Seibert et al., *J. Am. Chem. Soc.* 68, 2721 at 2722 (1946). The quinolinemethanol is reported to possess activity against Lophurae malaria in ducks. See. Wiselogle, *A Survey of Antimalarial Drugs*, 1941–1945, Volume 1, page 149, Table 17, (Published by J. W. Edwards, Ann Arbor, Mich., 1946).

The 5-bromo-4-phenylpyrimidine has fungicidal activity against *Trichophyton mentagrophytes* and against *Botrytis cinerea*.

I claim:

1. In the process for brominating pyrimidine by heating a mixture of bromine and pyrimidine hydrochloride at an elevated temperature, the improvement which comprises the steps of (1) mixing a hydrogen halide salt of pyrimidine with a solvent selected from the group consisting of nitrobenzene, o-dichlorobenzene, benzonitrile, and o-nitrotoluene, (2) heating and maintaining the mixture at a temperature in the range of from about 125° to about 135°C., (3) adding bromine to the heated mixture over a period of time of about 30 to about 90 minutes, and (4) maintaining the reaction mixture at a temperature of from about 125° to about 135°C. for an additional period of time of about 2 hours to about 6 hours.

2. The improved process of claim 1 wherein the solvent for step (1) is nitrobenzene.

3. The improved process of claim 1 wherein the solvent for step (1) is o-dichlorobenzene.

4. The improved process of claim 1 wherein the solvent for step (1) is benzonitrile.

5. The improved process of claim 1 wherein the pyrimidine hydrogen halide is selected from the group consisting of pyrimidine hydrochloride, pyrimidine hydrobromide and pyrimidine hydriodide.

6. The improved process of claim 1 wherein the pyrimidine hydrogen halide is pyrimidine hydrochloride.

* * * * *